United States Patent
Harrell

(10) Patent No.: US 9,907,821 B2
(45) Date of Patent: *Mar. 6, 2018

(54) AMNIOTIC FLUID FORMULATION FOR TREATMENT OF JOINT PAIN OR DISORDERS

(71) Applicant: MAM Holdings of West Florida, L.L.C., Tarpon Springs, FL (US)

(72) Inventor: Carl Randall Harrell, Tarpon Springs, FL (US)

(73) Assignee: MAM Holdings of West Florida, L.L.C., Tarpon Springs, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/289,367

(22) Filed: Oct. 10, 2016

(65) Prior Publication Data
US 2017/0100439 A1    Apr. 13, 2017

Related U.S. Application Data

(60) Provisional application No. 62/239,713, filed on Oct. 9, 2015.

(51) Int. Cl.
*A61K 35/50* (2015.01)
*A61K 45/06* (2006.01)
*A61K 9/00* (2006.01)
*A61K 9/08* (2006.01)
*A61J 1/05* (2006.01)

(52) U.S. Cl.
CPC ............... *A61K 35/50* (2013.01); *A61J 1/05* (2013.01); *A61K 9/0014* (2013.01); *A61K 9/0019* (2013.01); *A61K 9/08* (2013.01); *A61K 45/06* (2013.01)

(58) Field of Classification Search
None
See application file for complete search history.

(56) References Cited

U.S. PATENT DOCUMENTS

| | | |
|---|---|---|
| 1,699,479 A | 1/1929 | Scott |
| 3,752,158 A | 8/1973 | Kariher |
| 4,308,875 A | 1/1982 | Young |
| 4,977,897 A | 12/1990 | Hurwitz |
| 5,000,192 A | 3/1991 | Sealfon |
| 5,219,576 A | 6/1993 | Chu |
| 5,436,135 A | 7/1995 | Tayot |
| 5,698,228 A | 12/1997 | Takai |
| 5,997,896 A | 12/1999 | Carr, Jr. |
| 7,871,646 B2 | 1/2011 | Ghinelli |
| 7,928,280 B2 | 4/2011 | Hariri |
| 8,372,439 B2 | 2/2013 | Daniel |
| 9,132,156 B1 | 9/2015 | Werber |
| 2004/0057938 A1 | 3/2004 | Ghinelli |
| 2004/0093046 A1 | 5/2004 | Sand |
| 2005/0079147 A1 | 4/2005 | Delaey |
| 2008/0064098 A1 | 3/2008 | Allickson |
| 2008/0181935 A1 | 7/2008 | Bhatia |
| 2008/0181967 A1 | 7/2008 | Liu |
| 2008/0286378 A1 | 11/2008 | Behrens |
| 2009/0054350 A1 | 2/2009 | Tayot |
| 2010/0318048 A1 | 12/2010 | Hoefinghoff |
| 2011/0269667 A1 | 11/2011 | Shoseyov |
| 2012/0010727 A1 | 1/2012 | Young |
| 2014/0336600 A1 | 11/2014 | Harrell |
| 2015/0025366 A1 | 1/2015 | Harrell |

FOREIGN PATENT DOCUMENTS

| | | |
|---|---|---|
| WO | 2004026244 | 1/2004 |
| WO | 2006091546 | 8/2006 |
| WO | 2015134936 | 9/2015 |

OTHER PUBLICATIONS

Adzick, et al., "Cells, matrix, growth factors, and the surgeon. The biology of scarless fetal wound repair", Ann Surg, 220:10 8 (1994).
Ainslie, "Inhalational injuries produced by smoke and nitrogen dioxide", G, Respir Med. 87(3):169-74(1993).
Anker, et al., "Amniotic fluid as a novel source of mesenchymal stem cells for therapeutic transplantation", Blood, 102:1548 9 (2003).
Baur, et al., "Output and aerosol properties of 5 nebulizer/compressor systems with arformoterol inhalation solution", Respiratory Care, 54(10:1342-7 (2009).
Bergeron,et al.,"Airway remodeling in asthima: from benchside to clinical practice", Can Respir J., 17(4): e85-e93 (2010).
Biosis Database accession No. PREV200510252583, "Tropical application of amniotic fluid reduces corneal neovascularization after ocular alkali burn",1 page., appeared Apr. 1, 2004, retrieved Jul. 28, 2009.
Castro-Combs, et al., "Cornel wound healing is modulated by topical application of amniotic fluid in an exvivo organ culture model", Exp Eye Res., 87:56-63 (2008).
D'Agostino, et al., "Mesenchymal stem cell therapy for the treatment of chronic obstructive pulmonary disease", Expert Opin Biol Ther. 10(5):681-7 (2010).
Dua, et al., "A new classification of ocular surface burn", Br J Ophthalmol, 85:1379-83 (2001).
Duffy, et al., "Vascular Endothelial Growth Factor (VEGF) and Its Role in Non-Endothelial Cells: Autocrine Signalling by VEGF", In: Madame Curie Bioscience Database [Internet]. Austin (TX): Landes Bioscience (2000).
Fletcher, et al., "The natural history of chronic airflow obstruction", Br Med J. 1:1645-8 (1977).
Gao, et al., "Effects of amniotic fluid on proteases: a possible role of amniotic fluid in fetal wound healin", Ann Plastic Surg, 33:128 34 (1994).

(Continued)

*Primary Examiner* — Allison M Fox
(74) *Attorney, Agent, or Firm* — Pabst Patent Group LLP

(57) ABSTRACT

A human amniotic fluid formulation has been developed for administration into a joint or associated soft tissue such as a tendon or ligament for treatment of pain, degeneration or injury. The formulation is a sterile de-cellularized human amniotic fluid (D-HAF), devoid of amniotic stemcells and elements of micronized membrane or chorion particles, which has not been heat treated or treated with ethidium bromide. The formulation is optionally diluted, or concentrated, depending on the severity of the disorder or injury. Examples demonstrate efficacy in treatment of pain, disease, disorder, degeneration or injury of a joint or associated soft.

10 Claims, No Drawings

(56) References Cited

OTHER PUBLICATIONS

Gorguner, et al., "Acute inhalation injury", Eurasian J Med. 42(1):28-35(2010).
Gu,et al., "Mesenchymal stem cells alleviate airway inflammation and emphysema in COPD through down-regulation of cyclooxygenase-2 via p38 and ERK MARK pathways", Sci Rep. 5:8733 (2015).
Hartzell, "Overview of combustion toxicology", Toxicology.,115(1-3):7-23 (1996).
Herretes, et al., "Use of topical human amniotic fluid in the treatment of acute ocular alkali injuries in mice", Am J Ophthalmology, 142(2):271-8 (2006).
Hoeben, et al., "Vascular endothelial growth factor and angiogenesis", Pharmacol Rev, 56:549-80 (2004).
Hoyert, et al., "Deaths: preliminary data for 2011". Natl Vital Stat Rep. 61 (6):1-65 (2012).
International Search Report and Written Opinion for PCT/US206/056231 dated Dec. 6, 2016.
International Search Report and Written Opinion for PCT/US206/056267 dated Dec. 7, 2016.
Kales, et al., "Acute chemical emergencies", N Engl J Med., 19; 350(8):800-8 (2004).
Karacal, et al., "Effe t of human amniotic fluid on bone healing", J Surg Res., 129(2):283-7 (2005).
Lee, et al, "Effect of amniotic fluid in corneal sensitivity and nerve regeneration after excimer laser ablation", Cornea, 15(5):517-24 (1996).
Maraldi, et al., "Role of hepatocyte growth factor in the immunomodulation potential of amniotic fluid stem cells", Stem Cells Transl Med, 4(6):539-47 (2015).
Nagase, et al., "Structure and function of matrix metalloproteinases and TIMPs", Cardiovasc Res., 69(3): 562-73 (2006).
Nemery, "Metal toxicity and the respiratory tract", Eur Respir J. 3(2):202-19 (1990).
Newman, et al., "Occupational illness", N Engl J Med. 26; 333(17):1128-34 (1995).
Ozgenel, et al., "Effect of human amniotic fluid on peritendinous adhesion formation and tendon healing after flexor tendon surgery in rabits", J Hand Surg., 26(2):332-9 (2001).
Ozgenel, et al., "Effects of human amniotic fluid on cartilage regeneration from free perichondrial grafts in rabits", British J Plastic Surg., 57(5):423-8 (2004).
Ozgenel, et al., "Effects of human amniotic fluid on peripheral nerve scarring and regeneration in rats", J Neurosurg, 98:371 7 (2003).
Sporn, et al., "Transforming growth factor-beta: biological function and chemical structure", Science, 233(4763) 532-4 (1986).
Todderud, et al., "Epidermal growth factor: the receptor and its function", Biofactors., 2(1):11-5 (1989).
Weiss, et al., "placebo-controlled, randomized trial of mesenchymal stem cells in COPD", Chest. 143(6):1590-8 (2013).
Woode, et al., "Collagenolytic matrix metalloproteinases in chronic obstructive lung disease and cancer", Cancers, 7(1): 329-341 (2015).
Yun, et al., "Fibroblast growth factors: biology, function, and application for tissue regeneration", J Tissue Eng , 218142. doi:1-18 (2010).

AMNIOTIC FLUID FORMULATION FOR TREATMENT OF JOINT PAIN OR DISORDERS

CROSS-REFERENCE TO RELATED APPLICATIONS

This application claims benefit of U.S. Provisional Application No. 62/239,713, filed Oct. 9, 2015, which is incorporated by reference in its entirety.

STATEMENT REGARDING FEDERALLY SPONSORED RESEARCH

This invention was made without government support or Grants awarded by the National Institutes of Health. The government has no rights in the invention.

FIELD OF THE INVENTION

This generally relates to the treatment, prevention or alleviation of joint pain, disease, injury, disorder, or degeneration by administration of a formulated human amniotic fluid solution.

BACKGROUND OF THE INVENTION

Orthopaedic ailments and movement disorders have a direct causal impact on a person's ability to perform basic functions such as walking, reading, driving and other common activities. Good health contributes significantly to a person's quality of life and their ability to perform common daily activities and simple functions in their routine environments. Orthopaedic and movement disorders and diseases can be severely incapacitating, and occur in a wide variety of forms. Millions of people suffer from some form of movement ailment. As an example, torticollis, a condition in which the head becomes persistently turned to one side, is often associated with painful muscle spasms. The lives of individuals with this disorder are negatively impacted due to consistent pain and limited movement. Treatment for torticollis is targeted to relax the contracted neck muscles involved. Treatments include medication, physical devices, botulinum toxin, physical therapy, stretching exercises, and surgery. In most people, torticollis resolves in several days to a few weeks. A few people will develop continuing neck problems for months to years Acute and chronic pain, loss of structural function and range of movement can occur due to disease, injury, disorders (such as malalignment), or degeneration. There are two principle types of tissue involved: bony tissues, including joints and the collagenous surfaces thereon, and soft tissues such as ligaments, tendons, and capsules.

Treatment of degenerative joint disease (osteoarthritis) is discussed in relationship to pathogenesis of five clinical entities: 1) occurring in high motion joints and associated with synovitis; 2) associated with low motion joints; 3) "non-progressive" articular cartilage erosion; 4) secondary to other identified problems (intra-articular fractures, ligamentous damage, wounds, septic arthritis, osteochondrosis); and 5) chondromalacia of the patella. In addition to direct damage to articular cartilage, synovitis and capsulitis and depletion of matrical glycosaminoglycans and proteoglycans play important roles.

The natural healing response in damaged articular cartilage is inadequate. The principles of treatment are divided into: 1) prevention or treatment of primary causes. These include the effects of track surface, shoeing, and the appropriate resolution of intra-articular fractures, septic arthritis and osteochondritis dissecans. 2) treatment of active soft tissue disease contributing to articular cartilage degeneration, including rest, physical therapy, synovectomy and administration of anti-inflammatory drugs, sodium hyaluronate and polysulfated glycosaminoglycans. 3) treatment of articular cartilage loss or degeneration, including articular cartilage curettage, subchondral bone drilling, osteophyte removal, articular cartilage grafting and arthrodesis.

In sum, methods of treatment are limited to surgical procedures, palliative (injection of steroids or anesthetics), and injection of "repair promoters" such as hyaluronic acid, none of which are totally effective.

It is an object of the present invention to provide a formulation that can be used for the management of chronic joint pain, injury or disorders.

It is a further object of the present invention to provide a formulation that induces healing as well as increases joint mobility and decreases pain.

SUMMARY OF THE INVENTION

A human amniotic fluid formulation has been developed for treatment of joint disease, injury, pain or degeneration. The formulation is a sterile de-cellularized human amniotic fluid (D-HAF), typically administered by injection. D-HAF contains over 300 human growth factors. D-HAF is devoid of amniotic stemcells and elements of micronized membrane or chorion particles. The formulation may be diluted prior to administration, based on the severity of the disorder or injury.

D-HAF is prepared from human amniotic fluid from which the amniotic stem cells and particulate matter have been removed. In the preferred embodiment, the process consists of separating the cells from the AF using centrifugation and then filtering the supernatant through a series of filtration devices to remove all remaining cells and bioburden. Each lot is tested for bioburden and is certified sterile to contain <1 harmful organisms. The purified fluid is sterilized without the use of harsh terminal irradiation, e-beam or Ethylene Oxide (EO).

Methods for treating pain, disease, disorder, degeneration or injury of a joint or associated soft tissue using the D-HAF formulation are described. In some embodiments, the formulation is administered to treat joint conditions such as joints with pain, injury, degeneration, cartilage wear or tear, joints that have been fractured, arthritis, bursitis, dislocations, tendinitis, and tenosynovitis. In some embodiments, the formulation is administered to bones that have had prosthetic implants, pins, screws or plates attached or implanted into them, to promote healing and repair, and to reduce inflammation. In some embodiments, injections are administered to assist in resurfacing and repair or regeneration of cartilage. In some embodiments, the formulation is administered to assist in soft tissue repair, such as repair of torn or strained ligaments or tendons. In one embodiment, the formulation is administered by injection to joints, bursae, tendon sheaths, or soft tissues at/near the site of injury. In some embodiments, the formulation is injected into and/or adjacent to the joint to be treated, on an as-needed basis. In another embodiment, the formulation is sprayed onto, soaked into, or powder dispersed onto the implant or prosthetic. This can include matrices, implants and sutures.

Methods for treating pain, disease, disorder, degeneration or injury of a joint or associated soft tissue using the described formulation in combination with one or more therapeutic, prophylactic or diagnostic agents are also described. In some embodiments, antimicrobial agents, analgesic agents, local anesthetic agents, anti-inflammatory agents, immunosuppressant agents, anti-allergenic agents, enzyme cofactors, essential nutrients, growth factors, and/or combinations thereof are co-administered.

A kit containing one or more single, sterile units of D-HAF in fluid, or solid form, and instructions on how the dose is to be used for treatment of pain, disease, disorder, degeneration or injury of a joint or associated soft tissue is also developed. The kit can also include a unit dose of sterile water, saline or buffer for dilution. The kit is generally used by practitioners for patients with pain, disease, disorder, degeneration or injury of a joint or associated soft tissue.

DETAILED DESCRIPTION OF THE INVENTION

I. Definitions

"Active Agent," as used herein, refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder.

"Effective amount" or "therapeutically effective amount," refers to an amount of the D-HAF effective to alleviate, delay onset of, or prevent one or more symptoms, particularly of a disease or disorder of a joint.

"Control" refers to an experiment performed without the active ingredient, for example without sterile DHAF composition. In other examples, controls are ones receiving only tissue grafts, or implants without the DHAF composition. Controls are known in the art.

"Enhance", "increase", "stimulate", "promote", "decrease", "inhibit" or "reduce" are used relative to a control. Controls are known in the art. For example, an increase response in a subject or cell treated with a compound is compared to a response in subject or cell that is not treated with the compound.

"Growth factors" generally refer to a group of proteins or hormones that stimulate the cellular growth. Growth factors play an important role in promoting cellular differentiation and cell division, and they occur in a wide range of organisms.

"Pharmaceutically acceptable," refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Biocompatible" and "biologically compatible," generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer," as used herein, generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

"Nanoparticle," as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle," as used herein, generally refers to a particle having a diameter, such as an average diameter, from about 1 micron to about 100 microns, preferably from about 1 micron to about 50 microns, more preferably from about 1 to about 30 microns. The microparticles can have any shape. Microparticles having a spherical shape are generally referred to as "microspheres".

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size," as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Implant," as generally used herein, refers to a polymeric device or element that is structured, sized, or otherwise configured to be implanted, preferably by injection or surgical implantation, in a specific region of the body so as to provide therapeutic benefit by releasing one or more therapeutic, prophylactic or diagnostic agents over an extended period of time at the site of implantation.

"Hyaline cartilage" refers to the connective tissue covering the joint surface. By way of example only, hyaline cartilage includes, but is not limited to, articular cartilage, costal cartilage, and nose cartilage.

"Connective tissue" refers to any tissue that connects and supports other tissues or organs, and includes but is not limited to a ligament, a cartilage, a tendon, a bone, and a synovium of a mammalian host.

The term "in combination" refers to the use of more than one therapeutic agent. The use of the term "in combination" does not restrict the order in which said therapeutic agents are administered to a subject.

II. Compositions

Formulations of purified human amniotic fluid are provided. Typically, the formulations include diluted sterile de-cellularized human amniotic fluid (D-HAF), either in fluid form or solid form, for example, lyophilized powder, alone or in combination with appropriate excipients. Other active agents can be included. D-HAF contains over 300 human growth factors. D-HAF is devoid of amniotic stem cells and elements of micronized membrane or chorion particles.

A. Purified Amniotic Fluid Formulation

Amniotic fluid ("AF") contains nutrients and growth factors that facilitate fetal growth, provides mechanical cushioning and antimicrobial effectors that protect the fetus, and allows assessment of fetal maturity and disease. AF typically contains mixtures of growth factors, pro-inflammatory cytokines and anti-inflammatory cytokines, as well as a variety of macromolecules including carbohydrates, proteins and peptides, lipids, lactate, pyruvate, electrolytes, enzymes, and hormones.

In the preferred embodiment, the raw fluid directly collected from the source is not heat-treated, chemical-treated, fractionated to produce the disclosed formulations. In some embodiments, the formulation retains more than 50%, more than 60%, more than 70%, more than 80%, or preferably more than 90%, of the amniotic factors present in the raw fluid. In some embodiments, the formulations are not diluted with any additional solution. In other embodiments, the formulations are not concentrated relative to the raw fluid.

In some embodiments, the formulation is a diluted sterile de-cellularized human amniotic fluid (D-HAF). D-HAF contains over 300 human growth factors. D-HAF is devoid of amniotic stem cells and elements of micronized membrane or chorion particles. The purified fluid is sterilized without the use of harsh terminal irradiation, e-beam or Ethylene Oxide (EO). In the preferred embodiment, the process consists of separating the stem cells from the AF using centrifugation and utilizing a series of filtration devices to remove all remaining cells and bioburden. Each lot is tested for bioburden and is certified sterile to contain <1 harmful organism.

Generally, methods of preparing sterile de-cellularized amniotic fluids involve a series of centrifugation and filtrations steps. Preferred methods of preparing sterile de-cellularized amniotic fluid are described in detail in U.S. application Ser. No. 15/053,497.

1. Method of Obtaining Amniotic Fluid

In some embodiments, the amniotic fluid is collected in a sterile operating room environment during an elective C-section. Typically, the procedure is performed using an ultrasound device to provide guidance for the process of obtaining human fluid from the woman, inserting a blunt tip needle into the amniotic sac of the woman, attaching the blunt tip needle to a three-way stopcock, connecting a Luer lock syringe to the three-way stopcock, connecting a first end of a length of sterile tubing with the three-way stopcock, and collecting sterilely the amniotic fluid through the blunt tip needle and sterile tubing into a collection container.

In this embodiment, the sterile collection container can include a pump with a suction device, typically a low suction device or a spring loaded low suction device. The suction device is fluidly connected to an internal balloon. This embodiment further includes manually pumping up the internal balloon in the sterile collection container using the low suction device to allow a low-level suction and collection of the amniotic fluid.

In one embodiment, tools to obtain sterilely filtered human amniotic fluid from a woman, include a three-way stopcock, a sterile blunt tip needle aseptically attached to the three-way stopcock, a luer lock syringe aseptically connected to the three-way stopcock, a sterile tubing aseptically connected to the three-way stopcock, a collection container or a collection container including a pump with suction device connected with the sterile tubing, a set of filters having the pore size of about 5 μm to about 10 μm, a set of capsule or cartridge filters having the pore size of about 1 μm, a set of capsule or cartridge filters having the pore size of about 0.45 μm or 0.2 μm, a set of sterile syringes or vials to store the sterile filtered amniotic fluid and, optionally, operating instructions on using the kit to obtain sterilely filtered human amniotic fluid. The filters having the pore size of from about 5 μm to about 10 μm and the capsule or cartridge filters can be made from cellulose ester, glass fiber or nylon.

The sterile collection container may include a pump with a suction device, which may be a low suction device or spring loaded low suction device. The suction device may be fluidly connected to an internal balloon. The internal balloon may be pumped up in the sterile collection container using the low suction device to allow a low-level suction and collection of the amniotic fluid. The sterile collection container may include a vent having a cap.

In one embodiment, utilizing the incision site immediately prior to performing the C-section and with ultrasound guidance to protect the fetus and mother provides a minimal or no risk environment for collection. Collection is achieved via a low level suction established within a collection container and/or via gravity. Typically, after high speed centrifugation filtration with 5 to 10 μm filters (low protein binding filter) is used to complete the removal of cells and large particles. Submicron filtration is then conducted with 1 μm and 0.45 μm or/and 0.2 μm filters (low protein binding filter), two in a series connection, to remove gross contaminates. Under this condition, soluble growth factors will pass through this filter to achieve a semi-sterile condition, very low bioburden counts. If under a strict aseptic operation condition, a $10^{-3}$ sterility assurance level is achieved. A $10^{-6}$ sterility assurance level can be achieved by submicron filtration with a 0.22 μm filter (low protein binding filter) into sterile packaging to achieve a sterile product. The filtrate is monitored after each filtration step to determine which components were removed and then to determine which process to use to achieve the desirable product.

Cells, large particles and other undissolvables are removed from the human amniotic fluid by centrifuging or depth filtering the human amniotic fluid. In some embodiments, the human amniotic fluid is centrifuged at about 5,000 rpm to about 10,000 rpm for between about 30 minutes and about 60 minutes. In this embodiment filters of about 5 μm to about 10 μm are used for the first filtration. These are typically cellulose ester filters, glass fiber filters, nylon capsule filters or nylon cartridge filters. Filters with a pore size of 1.0 μm are capsule filters or cartridge filters, typically formed of poly ether sulfone, poly vinylidene fluoride or cellulose acetate membranes. Filters with a pore size of 0.45 μm or 0.2 μm are capsule filters or cartridge filters, typically formed of poly ether sulfone membrane filters, poly vinylidene fluoride or cellulose acetate membranes.

One may use membrane filters including or made of hydrophilic polyethersulphone (PES) to filter protein solutions. Filter disks for small volumes and different sizes of cartridges for larger volumes such as 1 litre and more. Hydrophobic membranes like PTFE which are designed for liquids devoid of proteins should not be used. Start with centrifugation at 5000 to 8000 rpm for at least 30 minutes. Next, the supernatant is filtered with a prefilter to remove residual protein aggregates and precipitates in suspension (AP20 can be used). If one directly uses a 0.6/0.2 μm filter, after prefiltration, one may experience slow filtration rates and the flow may stop too quickly. It may be desirable to make intermediate filtration steps using 1.2 μm and 0.8 μm membranes. Typically, a final filtration through 0.2 μm is necessary to get the best sterility assurance level and produce a sterile amniotic fluid for injections. The final filtrate can be stored in frozen condition at about −20° C. to about −80° C. for long term storage.

The sterile amniotic fluid can be lyophilized to yield a lyophilizate. The sterilely filtered amniotic fluid may be distributed in vials equipped with special rubber stoppers for sterile lyophilization. The lyophilization is carried out in a sterile environment. The rubber stoppers on the vials are then automatically pushed down in the freeze dryer to definitively close them. Finally an aluminum cap is sealed on each vial to protect its sterile content.

The lyophilizate can be irradiated by e-beam irradiation or gamma ray irradiation to insure the sterility. The lyophilized amniotic fluid may be stored at +4° C. or room temperature for at least one year without decrease of its biological activity.

The sterile lyophilized amniotic fluid may be reconstituted by adding the initial volume of sterile water to the powder in order to restore a transparent and homogeneous physiological liquid.

2. Sources of Amniotic Fluid Formulations

The amniotic fluid formulations are prepared from sterile human amniotic fluid obtained from a pregnant woman. Suitable sources, e.g. of human AF, include AF that is obtained from patients who are undergoing amniocentesis, patients who are undergoing a Caesarean section delivery, and patients undergoing normal delivery using a specially designed receptacle to collect the fluid after rupture of membranes.

The de-cellularized human amniotic fluid (D-HAF) formulations can be stored for long periods of time, allowing for a broad range of application methods, including distribution and storage as aerosols, solutions, powders, etc. In some embodiments, the sterile D-HAF is refrigerated at about 1° C. to about 10° C. for long-term storage. In a further embodiment, the sterile D-HAF is refrigerated at 4° C. for up to 12 months and more. Preferably, the long-term storage does not reduce the quantity of the total soluble proteins or factors present in the D-HAF. For some embodiments, the total soluble proteins retained after long-term storage in refrigerated conditions is about 10%, 20%, 30%, 40%, 50%, 60%, 70%, 80%, or 90% of the fresh D-HAF.

D-HAF formulations containing amniotic factors can be supplied as a clear one-part solution in a suitable container for storage at 4° C., or for storage at −20° C., or at −80° C. For example, liquid formulations in prefilled aliquots can be suitable for storage at 1-5° C., or for storage at −20° C., or at −80° C. The liquid formulation can be suitable for topical application in a nebulizer or an inhaler. In other embodiments, the fluid can be supplied as a kit that can be stored at 4° C., at −20° C., or at −80° C. until needed.

In some embodiments, D-HAF formulations use a final filtration through 0.2 μm is necessary to get the best sterility assurance level and produce a sterile amniotic fluid without any irradiation. In some embodiments, D-HAF formulations have a $10^{-6}$ sterility assurance level without irradiation. In other embodiments, lyophilisate derived from amniotic fluid through lyophilization may be irradiated by e-beam irradiation or gamma ray irradiation to add another guarantee for the final sterility of the powder. In some embodiments, D-HAF formulations are synthesized amniotic fluid to include all the known amniotic factors for the same therapeutic, and/or prophylactic properties in treating pain, disease, disorder, degeneration or injury of a joint or associated soft tissue.

The sterilely filtered human amniotic fluid contains growth factors. The growth factors include human growth hormone, transforming growth factor beta 1, vascular endothelial growth factor, epidermal growth factor, transforming growth factor beta 3, and growth differentiation factor 11 or combinations thereof.

B. Additional Therapeutic, Prophylactic or Diagnostic Agents

In some embodiments, sterile de-cellularized human amniotic fluid (D-HAF) is administered in combination with one or more additional therapeutic, diagnostic, and/or prophylactic agents to alleviate pain, facilitate healing, and/or reduce or inhibit scarring. In some embodiments, the composition may contain one or more additional compounds to relieve symptoms such as inflammation. Non-limiting examples include antimicrobial agents, analgesics, local anesthetics, anti-inflammatory agents, anti-oxidants, immunosuppressants, anti-allergenic agents, enzyme cofactors, essential nutrients and growth factors. Suitable therapeutic agents include but are not limited to antibiotics, cytokines, and growth factors such as fibroblast growth factor, hepatocyte growth factor, platelet-derived growth factor, vascular endothelial cell growth factor, and insulin-like growth factor. In some embodiments, the one or more agents are hyaluronic acid, or glycosaminoglycans.

The active agents can be a small molecule active agent or a biomolecule, such as a peptide or protein, sugar or polysaccharide, lipid, nucleic acid or combination thereof. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, one or more additional agents may be dispersed, dissolved or suspended in the formulation, the sterile decellularized amniotic fluid or pharmaceutically acceptable carrier.

The amount of a therapeutic generally depends on the tissue to be treated. Specific dosages can be readily determined by those of skill in the art. See Ansel, Howard C. et al. *Pharmaceutical Dosage Forms and Drug Delivery Systems* (6$^{th}$ ed.) Williams and Wilkins, Malvern, Pa. (1995). Alternatively, the sterile de-cellularized human amniotic fluid can be used in combination with cell delivery, for example, the delivery of stem cells, pluripotent cells, somatic cells, or combinations thereof.

In other embodiments, one or more therapeutic, prophylactic or diagnostic agent is administered prior to, in conjunction with, subsequent to, or alternation with treatment with the sterile de-cellularized human amniotic fluid.

The therapeutic, prophylactic or diagnostic agent may be present in its neutral form, or in the form of a pharmaceutically acceptable salt. In some cases, it may be desirable to prepare a formulation containing a salt of an agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704.

In some cases, the additional agent is a diagnostic agent imaging or otherwise assessing the site of application. Exemplary diagnostic agents include paramagnetic molecules, fluorescent compounds, magnetic molecules, and radionuclides, x-ray imaging agents, and contrast media.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

In some embodiments, sterile de-cellularized human amniotic fluid are used in combination with one or more antimicrobial agents. An antimicrobial agent is a substance that kills or inhibits the growth of microbes such as bacteria, fungi, viruses, or parasites. Antimicrobial agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

Other exemplary antimicrobial agents include iodine, silver compounds, moxifloxacin, ciprofloxacin, levofloxacin, cefazolin, tigecycline, gentamycin, ceftazidime, ofloxacin, gatifloxacin, amphotericin, voriconazole, natamycin.

In some embodiments, sterile de-cellularized human amniotic fluid is administered in combination with one or more local anesthetics. A local anesthetic is a substance that causes reversible local anesthesia and has the effect of loss of the sensation of pain. Non-limiting examples of local anesthetics include ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and any combination thereof. In other aspects of this embodiment, the sterile DHAF composition includes an anesthetic agent in an amount of, e.g., about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, about 5.0%, about 6.0%, about 7.0%, about 8.0%, about 9.0%, or about 10% by weight of the total composition. The concentration of local anesthetics in the compositions can be therapeutically effective meaning the concentration is adequate to provide a therapeutic benefit without inflicting harm to the patient.

In some embodiments, sterile de-cellularized human amniotic fluid is used in combination with one or more anti-inflammatory agents. Anti-inflammatory agents reduce inflammation and include steroidal and non-steroidal drugs. Suitable steroidal active agents include glucocorticoids, progestins, mineralocorticoids, and corticosteroids. Other exemplary anti-inflammatory agents include triamcinolone acetonide, fluocinolone acetonide, prednisolone, dexamethasone, loteprendol, fluorometholone, ibuprofen, aspirin, and naproxen. Exemplary immune-modulating drugs include cyclosporine, tacrolimus and rapamycin. Exemplary non-steroidal anti-inflammatory drug include ketorolac, nepafenac, and diclofenac.

In some embodiments, anti-inflammatory agents are anti-inflammatory cytokines. Exemplary cytokines are IL-10, TGF-$\beta$ and IL-35. Anti-inflammatory cytokines in the context of biomaterial implant, and tissue grafts are cytokine that induce an anti-inflammatory immune environment or suppress inflammatory immune environment. Activation of regulatory T cells, Tregs, is involved in the prevention of rejection, the induction and maintenance of peripheral tolerance of the allograft. Th17 cells are a subset of T helper cells which is characterized by the production of IL-17. Th17 cells have been suggested to play a role in allograft rejection. In some embodiments, cytokines to be added to the sterile DHAF compositions are those that induce Tregs activation (e.g. IL-25) and suppress Th17 activation (e.g. IL-10) for minimizing rejection.

In some embodiments, sterile de-cellularized human amniotic fluid is administered in combination with one or more growth factors. Growth factor, also known as a cytokine, refers to a protein capable of stimulating cellular growth, proliferation, and/or cellular differentiation. Non-limiting examples of growth factors include transforming growth factor beta (TGF-$\beta$), transforming growth factor alpha (TGF-$\alpha$), granulocyte-colony stimulating factor (GCSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF8), growth differentiation factor-9 (GDF9), acidic fibroblast growth factor (aFGF or FGF-1), basic fibroblast growth factor (bFGF or FGF-2), epidermal growth factor (EGF), vascular endothelial growth factor (VEGF) and hepatocyte growth factor (HGF).

In some embodiments, the sterile de-cellularized human amniotic fluid composition is administered in combination with one or more enzyme cofactors, and/or one or more essential nutrients. Exemplary cofactors include vitamin C, biotin, vitamin E, and vitamin K. Exemplary essential nutrients are amino acids, fatty acids, etc.

In some embodiments, the sterile de-cellularized human amniotic fluid composition further comprises at least one eukaryotic cell type not present in the original amniotic fluid. Some exemplary eukaryotic cell types include stem cells, mesenchymal stem cells, immune cells such as T lymphocytes, B lymphocytes, natural killer cells, macrophages, dendritic cells, or combinations thereof. In some embodiments, the cells used are cells that dampen inflammation response such as regulatory T cells.

C. Formulations

In some embodiments, the sterile D-HAF compositions are packaged, for example, into sterile dosage units which can be stored and distributed for use by attending physicians.

These lyophilized or fluid formulations can be in the form of sterile packaged syringes for injection, dropper bottles, tubes or vials of solution. The dosages for the injectables typically will be 0.1 cc, 0.25 cc, 0.5 cc, 1.0 cc, 2 cc, 5 cc, 10 cc, and 20 cc. The injectables can be administered at the site of injury. In one embodiment, the formulation is sprayed onto, soaked into, or powder dispersed onto the implant or prosthetic. The efficacy is determined by physician evaluations, patient self-evaluations, and Quality of life evaluations.

In the preferred embodiment, the amniotic fluid is administered without any other excipient.

However, the sterile amniotic fluid formulation can be administered in concentrated form, diluted with sterile water or buffer, formulated as a solution or suspension. It can include additional therapeutic, prophylactic or diagnostic agent, either in the solution or suspension, or as particles (nanoparticles, liposomes, microparticles) or implants.

Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

1. Solutions and Suspension

Numerous formulations are known and available. Solutions can be the sterile filtered amniotic fluid, concentrated or diluted with water, buffered saline, or an equivalent, or emulsified with lipid or oil. Emulsions are generally dispersions of oily droplets in an aqueous phase. There should be no evidence of breaking or coalescence. Suspensions contain solid particles dispersed in a liquid vehicle; they must be homogeneous when shaken gently and remain sufficiently dispersed to enable the correct dose to be removed from the container. A sediment may occur, but this should disperse readily when the container is shaken, and the size of the dispersed particles should be controlled. The active ingredient and any other suspended material must be reduced to a particle size small enough to prevent irritation and damage to the cornea. They may contain suitable additives, such as antimicrobial agents, antioxidants, and stabilizing agents.

When the solution is dispensed in a multidose container that is to be used over a period of time longer than 24 hours, a preservative must be added to ensure microbiologic safety over the period of use.

Ideally, the pH of should be physiological, for example, pH 7.4. However, the decision to add a buffering agent should be based on stability considerations. The pH selected should be the optimum for both stability of the active pharmaceutical ingredient and physiological tolerance. If a buffer system is used, it must not cause precipitation or deterioration of the active ingredient. The normal useful range is 6.5 to 8.5, although lower pH may be used. The final pH of the solution is often a compromise, because many drugs have limited solubility and stability at the desired pH of 7.4. Buffers or pH adjusting agents or vehicles can be added to adjust and stabilize the pH at a desired level. The buffers are included to minimize any change in pH during the storage life of the drug; this can result from absorbed carbon dioxide from the air or from hydroxyl ions from a glass container. Changes in pH can affect the solubility and stability of drugs; consequently, it is important to minimize fluctuations in pH. The buffer system should be sufficient to maintain the pH throughout the expected shelf-life of the product. Low concentrations of buffer salts are used to prepare buffers of low buffer capacity.

The preparation of aqueous solutions requires careful consideration of the need for isotonicity, a certain buffering capacity, the desired pH, the addition of antimicrobial agents and/or antioxidants, the use of viscosity-increasing agents, and the choice of appropriate packaging. Solutions are considered isotonic when the tonicity is equal to that of a 0.9% solution of sodium chloride. Tissue can usually tolerate solutions equivalent to 0.5-2% of sodium chloride.

Solutions that are isotonic are preferred. An amount equivalent to 0.9% NaCl is ideal for comfort and should be used when possible. There are times when hypertonic solutions are necessary therapeutically, or when the addition of an auxiliary agent required for reasons of stability supersedes the need for isotonicity. A hypotonic solution will require the addition of a substance (tonicity adjusting agent) to attain the proper tonicity range.

A widely used buffer solution is Sorensen's modified phosphate buffer. Sorensen's modified phosphate buffer is used for drugs needing pH values between the range of 6.5-8.0. This buffer uses two stock solutions, one acidic containing $NaH_2PO_4$, and one basic containing $Na_2HPO_4$. Other suitable buffers are well known by those skilled in the art such as acetate, borate, carbonate, citrate, and phosphate buffers.

In some instances, the formulation is distributed or packaged in a liquid form. Alternatively, formulations can be packed as a solid, obtained, for example by lyophilization of a suitable liquid formulation. The solid can be reconstituted with an appropriate carrier or diluent prior to administration.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, aerosols, sprays or emulsions may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as PURITE®), phenylmercuric acetate, chlorobutanol, sorbic acid, chlorhexidine, benzyl alcohol, parabens, thimerosal, and mixtures thereof.

Solutions, suspensions, or emulsions may also contain one or more excipients known art, such as dispersing agents, wetting agents, and suspending agents.

D. Kits

In some embodiments, the compositions are provided in a kit. Formulations are prepared using a pharmaceutically acceptable "carrier" composed of materials that are considered safe and effective and may be administered to an individual without causing undesirable biological side effects or unwanted interactions. These lyophilized or fluid formulations can be in the form of sterile packaged syringes for injection, or tubes or jars of solution. The dosages for the injectables will be 0.1 cc, 0.25 cc, 0.5 cc, 1.0 cc, 2 cc, 5 cc, 10 cc, and 20 cc. Typically the sterile DHAF compositions will be in a single dose unit, or in a kit with a first containing with liquid to rehydrate the dry components in a second component. These may include components for administration, such as syringe and an applicator such as a needle.

III. Methods of Administration

Methods of using sterile, de-cellularized human amniotic fluid compositions for therapeutic, diagnostic, and prophylactic applications, especially application to joints, tendons, ligaments, cartilage or other connective tissue are provided.

In certain embodiments, the compositions are administered to promote joint or cartilage repair, and/or regeneration in a subject compared to compositions and methods that do not incorporate the use of the sterile decellularized amniotic fluid. In more specific embodiments, the compositions and methods promote integration of implants or grafted tissues in a subject into the implanted/grafted region, and results in a better "take" and reduced rejection of the implants or grafted tissues. The compositions can be administered to tissues, joints, ligaments, tendons, cartilage, or connective tissue directly, or indirectly via a dressing, cement or glue or hydrogel for tissue repair.

The formulations can be administered to any mammal, including humans, livestock (horses, sheep, cattle, and pigs) as well as domestic animals (dogs and cats being the most common). The decellularized amniotic fluid is administered in a dosing regimen and for a period of time effective to provide healing or repair or regeneration.

The DHAF composition may be retained at the site of application for an extended period of time. For example, after administration, one or more therapeutic agent in the DHAF composition remains at the site of application for at least 6 hours, at least 12 hours, at least 1 day, at least 2 days, at least 3 days, at least one week, at least 2 weeks, at least 3 weeks, at least 4 weeks, at least 5 weeks, at least 6 weeks, at least 7 weeks, at least 2 months, at least 3 months, at least 6 months, at least 9 months, at least 1 year or more.

A. Disorders and Diseases to be Treated

The compositions and methods of use thereof are suitable for managing or treating any pain, disease, disorder, degeneration or injury of a joint or associated soft tissue in human patients as well in animals.

A joint is where two or more bones come together, like the knee, hip, elbow, or shoulder. Joints can be damaged by many types of injuries or diseases, including arthritis (inflammation of a joint), bursitis (inflammation of a fluid-filled sac that cushions the joint), and dislocations (injuries that force the ends of the bones out of position). Some exemplary joint disorders are effusion of unknown origin or suspected infection, crystalloid arthropathies, synovitis, arthritis including, but not limited to, inflammatory arthritis, and advanced osteoarthritis, and others affect the joint membranes themselves. Other types of joint conditions can benefit from the use of the compositions are those affect the tendons, cartilage, bursae, ganglion cysts, trigger points, neuromas, entrapment syndromes, fasciitis, and fluid within the joint (synovial fluid) such as bursitis, tendinitis, and tenosynovitis. In some embodiments, the compositions and methods of use thereof are for treating, and/or alleviating one or more symptoms of arthritis, bursitis, dislocations, tendinitis, and tenosynovitis.

Any joint condition may be treated, including joints with pain, arthritis, osteochondrosis, fibrous dysplasia, bone tumor, degeneration, cartilage wear or tear, and joints that have been fractured. In some embodiments, the formulation is administered to bones that have had prosthetic implants, pins, screws or plates attached or implanted into them, to promote healing, repair, and/or to reduce inflammation. In some embodiments, injections of the disclosed are administered to promote resurfacing, repair, and/or regeneration of cartilage. In some embodiments, intraarticular injection of the formulation to an arthritic joint space of a mammalian host results in regenerating hyaline cartilage. After the injections of the formulation, the percentage of hyaline cartilages repaired, and/or regenerated is about 5%, 10%, 20%, 30%, 40%, 50%, 60%, 70%, 80%, 90%, or more than 90% of the initially damaged, worn cartilage, in volume.

In some embodiments, the formulation is administered to assist in connective tissue repair. The connective tissue includes, but is not limited to, cartilage, ligament, tendon, a bone, and a synovium of a mammalian host. In some embodiments, the formulation is administered to assist in repair of torn or strained ligaments or tendons. In one embodiment, the formulation is administered by injection to joints, bursae, tendon sheaths, or soft tissues at/near the site of injury. In another embodiment, the formulation is sprayed onto, soaked into, or powder dispersed onto the implant or prosthetic. This can include matrices, implants and sutures.

B. Treating Joint Disorders in Animals

The formulations may be administered to animals as well as to humans to treat or alleviate pain, disease, disorder, degeneration or injury of a joint or associated soft tissue including tendons, ligaments. Preferred animals include dogs, cats, horses, as well as other animals that can be treated including livestock (cattle, sheep, swine, goats). In some embodiments, the animals in need of treatment have one or more joint conditions including arthritis, bursitis, tendinitis, and tenosynovitis.

The compositions and methods are useful for managing or treating joint disorders in horses. The formulation can be administered prophylactically or therapeutically. In many cases, regular administration is used to prevent further damage. Examples of horses requiring prophylactic treatment include racehorses, barrel, reining, and cutting horses, jumpers and dressage horses. Treatment for prophylaxis is typically done using a slightly lower dose and injected into the affected or at risk joints. A series of injections may be administered into or at the joint, tendons or ligaments for chronic injury.

The most common joint issues in dogs are hip dysplasia, elbow dysplasia and displaced patellas, as well as arthritis due to age or trauma. As in the case of the horses, treatment may be administered prophylactically, on a regular basis for chronic injury or escalated dosage for acute injury.

In all cases the formulation may be administered directly as in the case of surgery for an injury or implantation of a prosthetic, pins or screws.

All joint diseases that affect large animals produce some degree of inflammation, often with accompanying swelling, pain, redness or heat. Important arthritic conditions include traumatic arthritis, osteochondritis dissecans, subchondral cystic lesions, septic (infectious) arthritis, and osteoarthritis. In some embodiments, the compositions and methods of use thereof are for treating, alleviating one or more symptoms of traumatic arthritis, osteochondritis dissecans, subchondral cystic lesions, septic (infectious) arthritis, or osteoarthritis in animals such as horses and dogs.

In some embodiments, the compositions and methods of use thereof are for treating, and/or alleviating one or more symptoms of hip dysplasia, elbow dysplasia, or panosteitis in animals such as dogs. In some embodiments, the compositions and methods of use thereof are for treating, and/or alleviating one or more symptoms of disorders of the hip such as coxitis, dislocations, fractures, and bursitis in animals such as horses and dogs.

Common in horses, bursitis is an inflammatory reaction within a bursa that can range from mild inflammation to infection. True bursitis involves inflammation of a natural bursa, for example, fistulous withers, or poll evil. Fistulous withers is a condition in which the bursa in a horse's withers region (the ridge between the shoulder bones) becomes infected and inflamed. Poll evil is a virtually identical condition, except that the location of infection is the bursa behind the horse's ears in the area known as the poll. In each instance, a ruptured bursal sac creates an opening that makes the bursa susceptible to infection. In contrast, acquired bursitis is the development or inflammation of a bursa where none previously existed, as with capped elbow or hock. In capped elbow and hock, bursas beneath the hock and elbow can become inflamed if a horse suffers trauma from falling in or kicking its stall, from lying on poorly bedded hard floors, riding a trailer tailgate, wearing iron shoes that project beyond the heels, or from leaning or reclining for long periods of time. In some embodiments, the compositions and methods of use thereof are for treating, and/or alleviating one or more symptoms of bursitis in animals such as horses.

Tendinitis is the inflammation of a tendon. Tendon inflammation may be short-term (acute tendinitis), or build up over a period of time (chronic tendinitis). The condition is most common among horses that do fast work, such as racehorses. Tenosynovitis is an inflammation of the synovial membrane and usually the outer fibrous covering of the tendon. Possible causes include a response to traumatic injury or infection. When seen in young animals where the cause is uncertain, the condition is called idiopathic synovitis. In some embodiments, the compositions and methods of use thereof are for treating, and/or alleviating one or more symptoms of tendinitis, tenosynovitis, or idiopathic synovitis in animals such as horses.

The compositions and methods of managing or treating joint disorders in in dogs and cats are also disclosed. Some exemplary joint disorders in dogs and cats include arthritis, bursitis, tendinitis, and tenosynovitis. In some embodiments, the compositions and methods of use thereof are for treating, and/or alleviating one or more symptoms of joint disorders such as arthritis, bursitis, tendinitis, and tenosynovitis in dogs and cats. The most common signs of joint disease in dogs and cats include stiffness, limping, or favoring a limb—particularly after sleep or resting, inability to rise, reluctance to jump or even climb stairs, and noticeable pain.

C. Dosages and Dosing Regimen

Dosage and dosing regimens are dependent on the severity of the condition of joint and/or soft tissue to be treated, and are known to those skilled in the art. The formulation is tailored to the individual subject, the nature of the condition to be treated in the subject, and generally, the judgment of the attending practitioner. In yet another embodiment, the formulation is any amount of about 0.1 cc to 20 cc.

The standard protocol is a series of three injections that can be done daily, every other day, once a week, once a month, or quarterly, depending on the indication and on the severity of the injury or inflammation. In preferred embodiments, the larger hip and shoulder joints get 1.9 cc of PDA Human Amniotic Fluid and the smaller joints get 0.5 cc and the fingers and feet get 0.25 cc.

A filled ampoule contains a formulation of D-HAF. This is generally in a pharmaceutically acceptable carrier and buffered for use in human or animal subjects to a pH of about 3.5-10.0. The formulations of the examples are buffered to about pH 6.0-7.5. The formulations are free of preservative, which is an advantage as some preservatives can be associated with side effects such as synovitis. Water or saline solution is used to provide the carrier.

One or more tonicity adjusting agents may be added to provide the desired ionic strength. Tonicity-adjusting agents for use include those which display no or only negligible pharmacological activity after administration. Both inorganic and organic tonicity adjusting agents may be used.

Compositions can also include excipients and/or additives. Examples of these are surfactants, stabilizers, complexing agents, antioxidants, or preservatives which prolong the duration of use of the finished pharmaceutical formulation, flavorings, vitamins, or other additives known in the art. Complexing agents include, but are not limited to, ethylenediaminetetraacetic acid (EDTA) or a salt thereof, such as the disodium salt, citric acid, nitrilotriacetic acid and the salts thereof. In one embodiment, the complexing agent is EDTA. Preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E or salts or esters thereof.

In some embodiments, lyophilized D-HAF formulations are preferred. In some embodiments, the lyophilized D-HAF is reconstituted by adding the initial volume of water. In other embodiments, the formulation is further diluted to from about 1% to about 99% of the reconstituted D-HAF. The refrigerated formulation is readily diluted to from about 1% to about 99% of the original D-HAF to a desired concentration for applications.

In other embodiments, the final formulation is prepared as a much more concentrated solution depending on the need of application. In one embodiment, the lyophilized D-HAF is reconstituted by adding half of the initial volume of water to achieve twice as concentration solutions of all amniotic factors. In a further embodiment, the lyophilized D-HAF is reconstituted by adding 10% of the initial volume of water to achieve 10-fold more concentrated solutions of the amniotic factors for application. In some embodiments, the refrigerated D-HAF can be used to reconstitute the lyophilized D-HAF in order to obtain a more concentrated solution.

The D-HAF formulations can be administered as frequently as necessary and appropriate. The frequency generally depends on the severity of the joint/soft tissue condition, and the responsiveness of the target tissues to the treatment with D-HAF formulations. In some embodiments, the D-HAF formulations are administered on one-a-week basis. In other embodiments, the D-HAF formulations are administered on one-a-month basis. In some embodiments, the administration routine can change based on the practitioners assessment of the patient after the prior treatment.

Since there is no toxicity known to be associated with the formulation, it can be injected as often as the physician chooses, unlike steroids that can only be injected infrequently, typically two to three times a year.

The present invention will be further understood by reference to the following non-limiting examples.

EXAMPLES

The present invention will be further understood by reference to the following non-limiting examples. The examples showing preparation of human amniotic formulation are from US20150025366.

Example 1

Preparation of Human Amniotic Formulation

Materials and Methods

Human amniotic fluid is collected from selected caesarean sections, which make aspiration of the amniotic fluid in clean condition possible. Then the amniotic fluid is stored in refrigerated condition at 2° C. to 6° C. before the clarification and filtration process. The amniotic fluid is centrifuged at 5,000 to 10,000 rpm for 30 minutes to 1 hour in 50 mL to 250 mL swing out buckets. The supernatant is collected. When collecting the supernatant it is important to avoid detaching or aspirating insoluble components possibly coming from the pellet or from the fatty overlayer. If the supernatant still contains residual insoluble components, it may be pre-filtered with 5 to 10μ cellulose ester capsule pre-filters without TRITON® surfactant to avoid contamination in the filtration process. The liquid phase is collected and filtered with poly ether sulfone 1.0μ capsule filters and the liquid is collected. The liquid is then filtered with poly ether sulfone 0.2μ capsule filter. The filtrate is transferred to vials and sealed with stoppers aseptically. Four samples from the final filtrate are taken to test whether the sterile filtered human amniotic fluid retains growth factors, such as human growth hormone, transforming growth factor beta 1, vascular endothellal growth factor, epidermal growth factor, transforming growth factor beta 3.

The amniotic fluid from the final filtration is aseptically transferred to syringes or vials, then kept in a deep freezer at about −80° C. to about −20° C. for long term storage. The sterile amniotic fluid is dried in the vial via lyophilization in a built-in a sterile environment. The lyophilisate derived from the amniotic fluid is reconstituted with sterile water before its injection or topical administration. The lyophilisate can be stored at from +4° C. to about +25° C. (room temperature). All of this operation may be carried out in sterile condition and does not need additional sterilization methods such as a final irradiation.

If needed, the lyophilisate derived from amniotic fluid through lyophilization may be irradiated by e-beam irradiation or gamma ray irradiation to add another guarantee for the final sterility of the powder. Irradiation of a lyophilisate is much less denaturing for proteins and peptides than irradiating aqueous solutions, because the absence of water considerably reduces the production of reactive superoxide anions and their diffusion during irradiation. Such superoxide anions are the main cause of splitting peptide bonds and chemically modifying amino acids of protein and peptides. After lyophilization, the amniotic fluid is reconstituted by adding the initial volume of water. After gentle homogenization, the powder is quickly dissolved in about one minute.

Results

The results show retention of growth factors. The concentration of the growth factors in the sterile filtered amniotic fluid is from about 30 pg/mL to about 2500 pg/mL. Except the vascular endothelial growth factor in sample 2, the concentrations of all the factors in the four samples are in the range of 30-150 pg/mL. Although part of growth differentiation factor 11 is lost in centrifugation and filtration, the final sterile filtered amniotic fluid still retains about 17% to 29% of growth differentiation factor from the raw human amniotic fluid.

Example 2

Administration to Human Patients with Joint Disease or Disorders

A patient with Spasmodic Torticollis, an extremely painful chronic neurological disorder, was treated by injection of the formulation to treat a bilateral rotator cuff injury. The formulation significantly reduced pain and increased the rate of healing.

Example 3

Treatment of Severe Knee Pain

A 68 year old male with bi-lateral severe knee pain indicated the pain was a 9 or 10 on a pain scale from 0 to 10, with 0 being no pain and 10 being the worst pain. The pain also radiated down the legs from time to time. Flexibility was greatly hampered, with difficulty in putting on shoes.

The individual was treated with a series of platelet rich plasma ("PRP") and Hylauronic Injections, neither working very well. Pain was not lessened and mobility was not greatly improved.

After one injection with the human amniotic fluid into both knees, there was pain relief. Within a few days pain went from a 9 to 10 to a 2 to 3, and has improved since then. Mobility was substantially increased.

Example 4

Treatment of Foot

A patient was treated by injection following foot surgery to insert screws and realign the foot bones.

Swelling was significantly reduced. Pain was reduced from a 7-8 to a 3-4.

Example 5

Treatment of Neck Injury/Pain

Individual had a cheerleading injury in High School. No problem until entering her forties. MRI showed severe disc degeneration between L3 and L4. The pain was excruciating. Recommended treatment was steroid injections and Radio Frequency Ablation ("RF") and ultimately, surgery. Over the next five years the patient had steroid injections that did not work, and two RF treatments 18 months apart, that did help a little.

Patient was this injected with amniotic fluid formulation and again two weeks later and again two weeks later.

With five hours after the second injection, pain went from an 8 on the pain scale to a 4. After third injection, pain is at a 2 and very manageable without medication.

Example 6

Treatment of Osteoarthritis

Patient is stooped, with some finger deformation, and shoulder and knee problems. Patient has had a total right knee replacement, and is considering an operation to his left knee. He has not had any surgeries on his shoulder.

He received one injection to his left shoulder; a posterior approach. Prior to treatment patient was able to raise his arm until it was lateral to the ground, with no pain. Any higher caused pain, which became excruciating by the time arm was perpendicular to the ground. A previous steroid injection provided no pain relief or increase in mobility.

After treatment there is full mobility of arm with no pain.

Example 7

Treatment of Osteoarthritis with Cartilage Regeneration

A 62-year old male with degenerative osteoarthritis of the left knee was treated. After treatment, Multiplanar, multi-sequence Magnetic Resonance Imaging of the left knee was performed without intravenous contrast. Recommended sequences from the International Society of Cartilage Repair were performed, which included the addition of a 3-D T1 weighted GRE sequence in addition to standard departmental knee MRI protocol.

MRI findings indicated that there had been interval rupture of the anterior cruciate ligament (ACL) but the PCL, MCL, and LCL are intact. The quadriceps and patellar tendons were intact. Complex tearing of the medial meniscus was noted but the lateral meniscus remains intact. There was no evidence of muscular tear, muscle strain, or muscle atrophy There was popliteus bursitis, less extensive than the prior study. There was a small loose body within the popliteus bursa measuring 5×8 mm; there was a small joint effusion, which was similarly decreased from the prior study; there was debris within the joint effusion, which could represent synovitis; and there was still cartilage loss in the medial compartment with subchondral marrow signal changes. There was complete regeneration of an area of focal cartilage loss along the anterior aspect of the lateral femoral condyle and restoration of normal subchondral marrow signal The lateral compartment articular cartilage was intact. There had been no progression of the loss of articular cartilage along the medial patellar face. The remaining articular cartilage in the patellofemoral compartment was intact. There were tricompartmental osteophytes, most pronounced in the medial compartment. There were small marginal osteophytes arising from the lateral and patellofemoral compartments. There was no evidence of acute fracture, dislocation, or destructive bony lesion.

Radiologist interpretation of the MRI results include: 1) Complete regeneration of an area of focal cartilage loss along the anterior aspect of lateral femoral condyle and restoration of normal subchondral marrow signal. The lateral compartment articular cartilage was completely intact. There had been no progression of loss of the articular cartilage along the medial patellar facet. There was persistent cartilage loss in the medial compartment with subchondral marrow signal changes. 2) Interval rupture of the ACL. Complex tearing of the medial meniscus was again observed. 3) Interval decrease in size of anterior knee effusion. Only a tiny knee effusion remained. Interval decrease in size of fluid within the popliteal bursa. A small loose body was within the popliteal bursa.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method of treating or alleviating pain or inflammation associated with a disease, disorder, degeneration or injury of a joint or associated soft tissue in a subject suffering therefrom comprising administering to or adjacent to the joint or soft tissue in the subject an effective amount of a sterile, de-cellularized, filtered human amniotic fluid (D-HAF) devoid of amniotic stem cells, elements of micronized membrane, and chorion particles, sterilized only by filtration.

2. The method of claim 1 wherein the D-HAF is administered in a form selected from the group consisting of a solution, suspension and powder.

3. The method of claim 2 wherein the D-HAF is administered with an implant, prosthetic, suture, pin, screw or plate, or soft tissue repair device.

4. The method of claim 1 wherein the D-HAF is administered with a pharmaceutically acceptable carrier for injection.

5. The method of claim 1 wherein the D-HAF is administered in combination with one or more additional therapeutic, prophylactic or diagnostic agents.

6. The method of claim 5 wherein the D-HAF is administered in combination with one or more agents selected from the group consisting of antimicrobial agents, analgesic agents, local anesthetic agents, anti-inflammatory agents, anti-oxidant agents, immunosuppressant agents, anti-allergenic agents, enzyme cofactors, essential nutrients, growth factors, and combinations thereof.

7. The method of claim 1 wherein the disorder is selected from the group consisting of arthritis, bursitis, tendinitis, tenosynovitis, osteochondrosis, fibrous dysplasia, bone tumor, dislocations, and fractures.

8. The method of claim 7 wherein the disorder is osteoarthritis.

9. The method of claim 1 wherein the D-HAF promotes repair, and/or regeneration of cartilage.

10. The method of claim 1 wherein the subject is selected from the group consisting of human, dog, cat, cow, horse, and domestic livestock.

* * * * *